United States Patent [19]

Pilkington et al.

[11] Patent Number: 4,739,654

[45] Date of Patent: Apr. 26, 1988

[54] METHOD AND APPARATUS FOR DOWNHOLE CHROMATOGRAPHY

[75] Inventors: Paul E. Pilkington, Houston, Tex.; Mark P. DiStefano; Marvin C. Allen, both of Ponca City, Okla.

[73] Assignee: Conoco Inc., Ponca City, Okla.

[21] Appl. No.: 916,751

[22] Filed: Oct. 8, 1986

[51] Int. Cl.⁴ ............................................. E21B 49/10
[52] U.S. Cl. .................................. 73/155; 73/61.1 C
[58] Field of Search .................. 73/61.1 C, 23.1, 155

[56] References Cited

U.S. PATENT DOCUMENTS

| | | | |
|---|---|---|---|
| 2,983,586 | 5/1961 | Blanchard | 73/155 |
| 3,254,531 | 6/1966 | Briggs | 73/155 |
| 3,386,286 | 6/1968 | Moore | 73/23.1 X |
| 3,462,761 | 8/1969 | Horeth et al. | 73/21.3 X |
| 3,577,782 | 5/1971 | Aitken | 73/155 |
| 3,611,799 | 10/1971 | Davis | 73/423 A |
| 3,795,149 | 3/1974 | Gillette et al. | 73/155 |
| 4,210,018 | 7/1980 | Brieger | 73/155 |
| 4,416,152 | 11/1983 | Wilson | 73/155 |

Primary Examiner—Jerry W. Myracle
Attorney, Agent, or Firm—Richard K. Thomson

[57] ABSTRACT

Method and apparatus for downhole chromatography. A tool housing includes a chromatograph and a formation tester for extracting a fluid sample from a formation adjacent the wall of an uncased well bore. When such a sample is extracted it is directed into the chromatograph which analyzes the same and transmits the information to the surface. Thereafter, solvent from a reservoir in the housing is used to purge the chromatograph to enable the tool to be relocated to a different level for additional formation fluid analysis.

20 Claims, 2 Drawing Sheets

METHOD AND APPARATUS FOR DOWNHOLE CHROMATOGRAPHY

BACKGROUND AND SUMMARY OF THE INVENTION

1. Field of the Invention

The instant invention relates to chromatographic methods and apparatus for analyzing formation fluids and more particularly to such methods and apparatus wherein a downhole tool extracts a formation fluid sample in an uncased well bore.

2. Setting of the Invention

After drilling an oil well, it is desirable to evaluate the formation to determine whether or not sufficient oil or gas can be produced to justify the expense of completing the well with casing and production tubing.

One way to determine composition of reservoir fluids is to run a drill stem test. Such a test entails running a string of drill pipe having a packer suspended near the lower end thereof into the well bore. The bore is packed off just above the zone of interest and fluid from the formation is permitted to flow into the drill stem. The pressure of the flow is monitored and a sample is collected in the drill pipe. Thereafter, the drill string is raised and the sample is analyzed by injecting some of the sample fluid into a chromatograph. The drill stem test suffers from several drawbacks. First, it is expensive and time consuming to run in a string of drill pipe to the formation of interest. Secondly, when fluid samples are collected they tend to separate and must be recombined at the surface. A more accurate analysis could be obtained if the formation fluid could be analyzed prior to separation into gas and liquid phases. Also, if the well bore is in relatively soft rock a drill stem test cannot be run without casing the well bore thus adding a substantial additional expense to the cost of the test.

There are prior art formation testers which can be lowered into an uncased well bore on a wire line to a level adjacent a formation of interest. Thereafter, a sample pad is firmly engaged against the wall of the borehole and formation fluid is drawn through a conduit in the pad into the tool. Then, the tool is raised to the surface and the collected sample is analyzed in a chromatograph to determine the composition of the formation fluids. Formation testers are typically large and include either one large chamber or multiple smaller chambers for collecting samples at different levels in the well bore. A problem which exists with prior art formation testers is that the initial flow from the formation is filtrate which includes drilling mud particles and the like which become lodged in the formation adjacent the borehole during the drilling process. This presents a special problem when an oil based drilling mud is used since the presence of oil in the mud can show up in a chromatograph analysis and be mistaken for connate fluid from the formation. There is at least one prior art tester in which filtrate flow is received into a first chamber while resistivity of the flow is measured. When resistivity stabilizes, thus indicating presence of connate flow, the flow is diverted into a second chamber and the tester retrieved to the surface.

Prior art devices for collecting formation fluid samples are susceptible to collecting contaminated samples due to filtrate flow. Such devices are also limited in the total number of samples which can be taken without being retrieved to the surface. In addition such devices are typically quite long to accomodate multiple chambers. When a single sample at a single level is to be collected, the device is generally still long to accomodate a large chamber so that at least some of the flow into the chamber, following the initial filtrate flow, will comprise connate formation fluid. In addition to these drawbacks, by the time the fluid sample is retrieved to the surface and prepared for analysis in a chromatograph, it will have separated into its gas and liquid phases and must be recombined as in the case when a fluid sample is obtained via a drill stem test.

The method of the instant invention comprises the steps of lowering a chromatograph into a well bore to a level at which fluids of interest are contained in the formation adjacent the chromatograph. A fluid sample is extracted from the adjacent formation and is directed into the chromatograph which generates information relating to the composition of the sample. Such information is transmitted to the surface thus providing an immediate indication of the makeup of the fluid sample. In one aspect of the invention, formation fluid is withdrawn and the resistivity thereof is monitored until it stabilizes thereby assuring that a connate fluid sample is analyzed by the chromatograph. In another aspect of the invention, the chromatograph is purged with a solvent subsequent to testing at a selected level thereby permitting movement of the chromatograph to a different level for testing another fluid sample.

The apparatus of the invention performs the steps of the method.

The instant invention provides a method and apparatus in which a plurality of connate formation fluid samples may be taken at different selected levels in a well bore.

The instant invention provides such a method and apparatus in which the fluid samples may be analyzed by a downhole chromatograph and, in one aspect of the invention, the information generated thereby transmitted to the surface.

In another aspect of the invention, the chromatograph is purged with a solvent between each fluid sample analysis.

Numerous advantages to the instant method and apparatus will become apparent to a person having ordinary skill in the art as the following detailed description is read in view of the accompanying drawings wherein.

DETAILED DESCRIPTION OF THE PREFERRED EMBODIMENT OF THE INVENTION

Indicated generally at 10 is a tool constructed in accordance with the apparatus of the instant invention. Tool 10 is shown received in a well bore 12 formed in a formation 14. The tool is suspended from the surface (not visible) by a wire line 16, such also including an electrical cable for providing electrical connections between the surface and components in tool 10 as will later be hereinafter more fully described.

Figure 1:
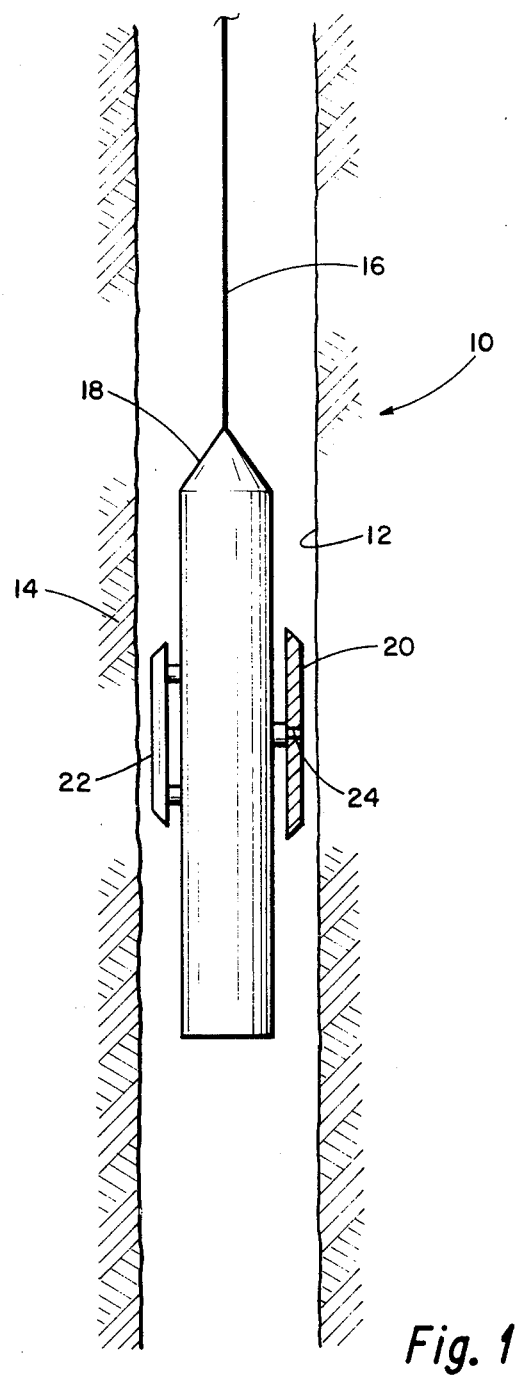
FIG. 1 is a somewhat schematic illustration of a tool constructed in accordance with the apparatus of the instant invention received in a well bore.

Tool 10 includes therein a housing 18. A sample pad 20 is extendable radially from the housing and is shown in FIG. 1 in a partially extended position. On the opposite side of tool 10 from sample pad 20 is a bracing pad 22, such being also radially extendable from the housing. When pads 20, 22 are completely extended, the radially outer surface of each pad is in flush engagement with the walls of well bore 12 thus anchoring the tool in the well bore.

Sample pad 20 includes a sample conduit 24 which, when pad 20 is engaged against the well bore wall, provides fluid communication between the fluids in formation 14 and the interior of housing 18.

Generally speaking, in the operation of tool 10, the tool is lowered to a selected level in the well bore and a formation fluid sample is provided to the interior of housing 18. The sample is processed by a chromatograph in the housing and information relating to the composition of the fluid sample is transmitted to the surface. Thereafter the chromatograph is purged with solvent from a reservoir received in housing 18 and the tool is moved to another location for additional fluid sample analysis.

Figure 2:
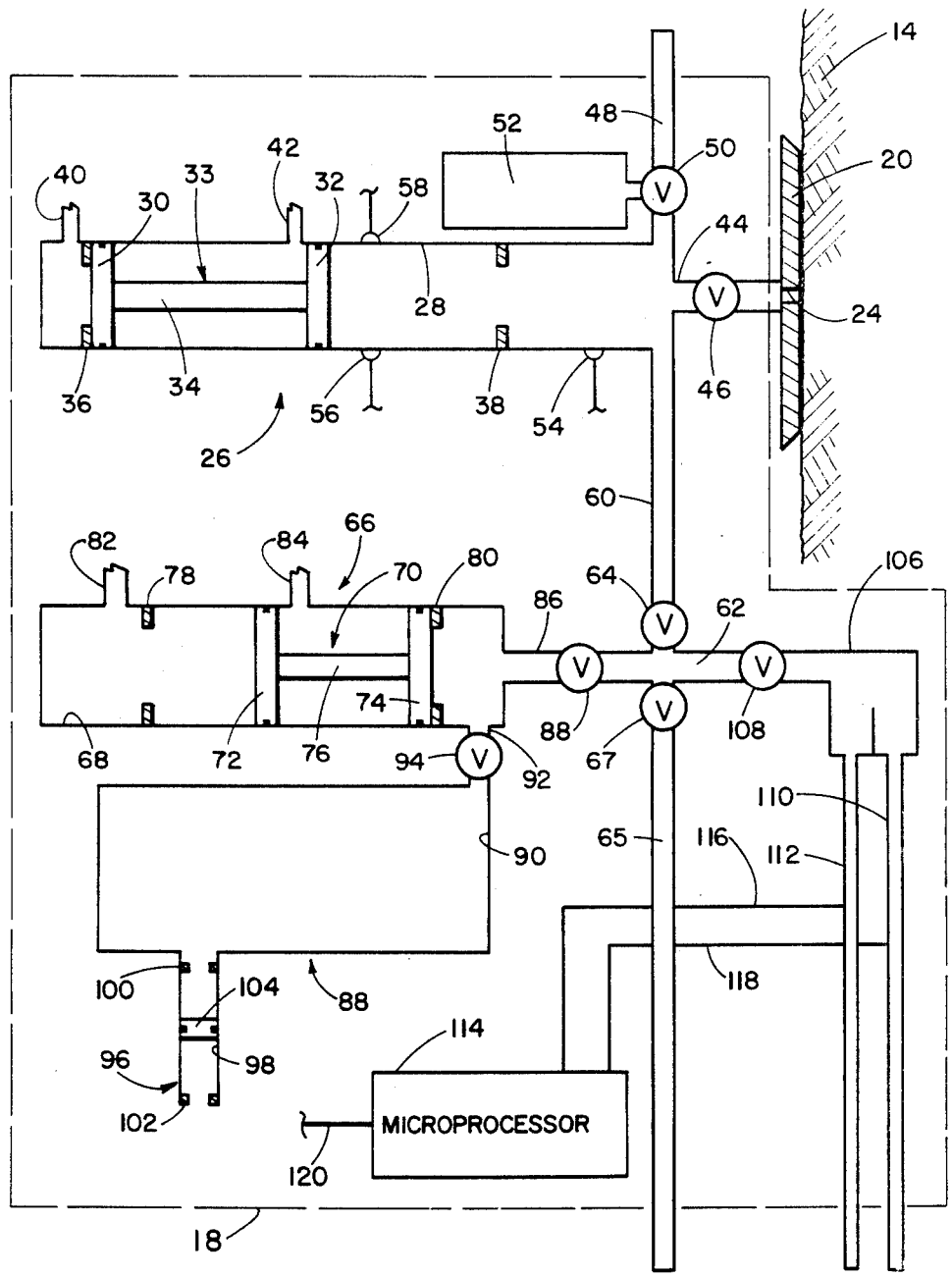
FIG. 2 is a schematic illustration of the tool of FIG. 1.

Turning now to FIG. 2, consideration will now be given to the structure received within housing 18. Included therein is a formation tester indicated generally at 26, such being also referred to herein as extracting means and as a purging chamber. The purging chamber includes a cylinder 28 having a piston-and-rod assembly, indicated generally at 33, slidably disposed therein. Assembly 35 includes a pair of slidable pistons 30, 32 received in cylinder 28 with the pistons being linked by a rod 34. Piston stops 36 define a first axial travel limit for assembly 33 while piston stops 38 define a second axial travel limit for the assembly. Cylinder 28 is in fluid communication with a pair of fluidic control ports 40, 42 which are in turn connected to conventional fluidic control circuitry (not shown) for driving assembly 33 between stops 36, 38. The fluidic control circuitry causes such movement under control of electrical signals from the surface which are transmitted to the tool via the electrical cable contained in wire line 16.

A conduit 44 is in fluid communication with the right end of cylinder 28 and includes therein a valve 46 for selectively shutting off or permitting flow through conduit 44. Conduit 44 is in fluid communication with sample conduit 24 in sample pad 20. Thus, when the sample pad is abutted against the well bore wall and valve 46 is opened, fluid in formation 14 can flow through conduits 24, 44 into cylinder 28.

Each of the valves in FIG. 2, like valve 46, may be selectively opened and closed by electrical signals which are transmitted to the tool via the electrical cable in wire line 16.

Another conduit 48 has one end in fluid communication with cylinder 28 and includes therein a valve 50. The other end of conduit 48 is in fluid communication with the well bore. Valve 50, like the other valves in the tool, operates in response to control signals from the surface; however, valve 50 is a three-way valve and may be oriented to permit fluid communication between cylinder 28 and the well bore or between cylinder 28 and a sample chamber 52 or may be oriented to block off fluid communication between cylinder 28, sample chamber 52, and the well bore.

Cylinder 28 has mounted thereon a resistivity probe 54, a temperature probe 56, and a pressure sensor 58. The resistivity probe measures the resistivity of fluid in cylinder 28 by applying a voltage across the fluid and measuring the current which passes therethrough. The temperature sensor monitors the temperature of the fluid while the pressure sensor monitors fluid pressure. The data from each of these monitoring devices is transmitted to the surface via the electrical cable in the wire line.

Continuing now the description of the preferred embodiment of the invention, a conduit 60 connects cylinder 28 to a chromatograph sample chamber 62 via a valve 64 which can selectively prohibit or permit flow in conduit 60. Valve 64 is referred to herein as first valve means. A conduit 65 has one end in fluid communication with chamber 62 and includes therein a valve 67. The other end of conduit 65 is in fluid communication with the well bore.

Indicated generally at 66 is an expansion chamber, such also being referred to herein as withdrawing and injecting means. Expansion chamber 66 includes a cylinder 68 having a piston-and-rod assembly 70 slidably disposed therein. Assembly 70 includes a pair of pistons 72, 74 connected by a rod 76. Piston stops 78, 80 define the axial limits of travel of assembly 70. Fluid ports 82, 84 are connected to conventional fluidic control circuitry (not shown) for moving assembly 70 between piston stops 78, 80. The fluidic control circuitry causes such movement under control of electrical signals from the surface which are transmitted to the tool via the electrical cable contained in wire line 16. Expansion chamber 66 is connected to a conduit 86 which, via valve 88, may be placed in fluid communication with chromatograph sample chamber 62.

Indicated generally at 88 is a solvent reservoir. The solvent reservoir includes a chamber 90 which is filled with a conventional solvent. The reservoir is connected to cylinder 68 by a conduit 92 having a valve 94 therein. Chamber 90 is in fluid communication with a pressure equalization device 96. The pressure equalization device includes a cylinder 98 in fluid communication with chamber 90. Cylinder 98 includes at either end thereof a pair of piston stops 100, 102 which define axial limits of travel for a slidable piston 104 received in cylinder 98. The pressure equalization device permits solvent in chamber 90 to be withdrawn therefrom as will later be hereinafter more fully described.

Chromatograph sample chamber 62 may be selectively placed in fluid communication with a conventional chromatograph 106 via a valve 108, such being also referred to herein as third valve means. Chromatograph 106 receives a fluid sample for analysis through valve 108 and provides the sample to a liquid chromatograph 110 and to a gas chromatograph 112. As a sample passes through the liquid and gas chromatographs, sensors in the liquid and gas chromatographs provide information relating to the composition of the gas and liquid to a microprocessor 114 via electrical conductors 116, 118. The microprocessor includes an output applied to electrical conductor 120 which transmits information relating to the composition of the fluid passed through the chromatograph to the surface on the electrical cable in the wire line.

In operation, tool 10 is suspended on wire line 16 at the surface of well bore 12 and is lowered to a level in the well bore at which it is desired to analyze fluid contained in formation 14 adjacent the tool. Thereafter, bracing pad 22 and sample pad 20 are radially extended from the tool thereby bracing the tool in the well bore and abutting the sample pad against the wall of the well bore as shown in FIG. 2.

Next, assembly 33 in formation tester 26 is urged to its right most position by introducing fluid in conduit 40 while valve 50 is in position for providing communication between cylinder 28 and the well bore. When assembly 33 is in its right most position, valve 50 is closed and valve 46 is opened thus placing sample conduit 24 in fluid communication with cylinder 28. Next, fluid is introduced into port 42 thereby urging assembly 33 back to the position shown in FIG. 2 and withdrawing formation fluid into the cylinder to the right of piston 32. The resistivity of the sample is noted, valve 46 is closed, valve 50 is opened and the assembly is again moved to the right to discharge the collected sample into the well bore. Thereafter, valve 50 is closed, valve 46 is opened and another formation fluid sample is withdrawn into the cylinder as before and the resistivity is again noted. The withdrawn sample is again discharged to the well bore and the process is repeated until the resistivity of successive samples is substantially equal thus indicating the presence of connate formation fluids. At this point, if desired, valve 50 may be oriented to provide communication between cylinder 28 and sample chamber 52 while assembly 33 is moved to the right thus storing a sample in chamber 52 which may be collected at the surface.

In any event, once a sample of connate formation fluid is in cylinder 28, valve 64 is opened thus permitting the sample to flow into chromatograph sample chamber 62. Thereafter valve 64 is again closed.

Next, valves 88, 94 are opened and assembly 70 is urged to the left by introduction of fluid into port 84. Such movement of assembly 70 withdraws solvent from chamber 90 and mixes the same with the fluid sample in chromatograph sample chamber 62. Next, valve 94 is closed and valve 108 is opened. When the piston is extended, the fluid sample mixed with solvent is injected into chromatograph 106 and from there through liquid chromatograph 110 and gas chromatograph 112 into the well bore. As the sample passes therethrough, information relating to the content of the liquids and gasses therein appears on electrical lines 116, 118 and is provided thereby to the microprocessor. The microprocessor transmits the information to the surface via electrical line 120.

After the sample passes through the chromatograph, valve 108 is closed and valve 94 is opened. Thereafter assembly 70 is moved to its left most position thus withdrawing solvent into cylinder 68. Then valve 94 is closed, valve 108 is opened, and assembly 70 is moved to its right thus forcing solvent through chromatograph sample chamber 62 and liquid and gas chromatographs 110, 112.

The structure of the apparatus is in the configuration of FIG. 2 after assembly 70 is moved to the right to force the sample in chamber 62 through the chromatograph. Now, valve 108 is again closed, valve 92 opened and assembly 70 again moves to the left thereby withdrawing solvent. Valve 94 is next closed and valve 108 opened thereby enabling another dose of solvent to be urged, under power of assembly 70, through chromatograph sample chamber 62 and the gas chromatograph. This process is repeated as many times as necessary to purge the chromatograph of any remaining traces of the fluid sample. Monitoring the chromatograph information at the surface for each dose of solvent passed therethrough enables an operator to determine when all traces of fluid sample are purged from the chromatograph. If it is desired to purge chamber 62 without purging chromatograph 106, the foregoing process may be repeated with valve 67 being closed and opened in lieu of valve 108. Such might be desirable when the fluid sample is purged from the chromatograph and a contaminated or otherwise undesirable sample is received in chamber 62.

Once the chromatograph is purged, the operator may open valve 64 thus providing additional fluid from cylinder 28 into chromatograph sample chamber 62 for another analysis. Alternatively, chamber 28 may be purged by forcing fluid therein through conduit 48 into the well bore and another fluid sample may be withdrawn from formation 14.

After sufficient samples are taken and analyzed, sample pad 20 and bracing pad 22 are retracted radially inwardly toward housing 18 and the tool is moved via wire line 16 to a different level in the well bore. Thereafter, the sample and bracing pads are extended thereby supporting the tool for additional testing at the new location. This process, i.e., testing at different selected levels, may be repeated at as many different levels as desired.

In a second embodiment of the tool, microprocessor 114 is programmed to open and close the various valves in the tool. Initially, the resistivity signal generated by resistivity probe 54 is provided to the microprocessor which is programmed to control valves 46, 50 and the fluidic controls attached to ports 40, 42 to repeatedly withdraw and discharge fluid samples as described above until the resistivity of the fluid samples stabilizes. When the resistivity is stablized, the additional valves in the tool, including the fluidic controls connected to ports 82, 84, are operated under computer program control in order to provide the sample to the chromatograph as described above. During chromatograph purging, the microprocessor is programmed to purge as many times as necessary until the electrical signals generated by the chromatograph indicate all traces of the fluid sample have been flushed from the chromatograph. A person having ordinary skill in the art can program the microprocessor to perform as described.

In yet another embodiment of the invention, liquid chromatograph 110 and gas chromatograph 112 may be replaced by a single chromatograph constructed for super critical chromatography thereby enabling analysis of both gas and liquid samples by a single chromatograph.

It can thus be seen that the instant invention provides a method and apparatus in which fluid formation chromatography results may be known almost immediately after withdrawal of the sample from the formation. Moreover, since the solvent purges the chromatograph after each use, the method and apparatus of the invention provides accurate chromatograph analyses even in the presence of oil-based drilling mud. In addition, the tool of the instant invention is relatively compact since there is no need for providing multiple sample chambers for collecting samples at different levels or for providing a single large sample chamber in order to accomodate initial filtrate flow from the formation before receiving connate fluid flow in the chamber.

It is to be appreciated that additions and modifications may be made to the embodiments disclosed herein without departing from the spirit of the invention which is defined in the following claims.

We claim:

1. A method for analyzing fluids contained in a formation traversed by a well bore comprising the steps of:
    lowering a chromatograph into the well bore to a level at which fluids of interest are contained in the formation adjacent the chromotograph;

extracting a fluid sample from the adjacent formation; and directing the sample into the chromatograph thereby generating information relating to the composition of the sample.

2. The method of claim 1 wherein said method further comprises the step of transmitting such information to the surface.

3. The method of claim 1 wherein the step of extracting a fluid sample from an adjacent formation comprises the step of withdrawing fluid from the formation into a first chamber and wherein said method further includes the step of placing said first chamber in fluid communication with a chromatograph sample chamber after the step of withdrawing fluid from the formation into said first chamber and prior to directing the sample into the chromatograph.

4. The method of claim 3 wherein the step of directing the sample through the chromatograph comprises the steps of:

removing the chromatograph sample chamber from fluid communication with said first chamber; and thereafter placing said chromatograph sample chamber in fluid communication with said chromatograph.

5. The method of claim 4 wherein said method further includes the step of placing said chromatograph sample chamber in fluid communication with a solvent reservoir prior to the step of placing said chromatograph sample chamber in fluid communication with said chromatograph.

6. The method of claim 4 wherein said method further includes the step of placing said chromatograph sample chamber in fluid communication with a solvent reservoir after the step of placing said chromatograph sample chamber in fluid communication with said chromatograph.

7. The method of claim 1 wherein the step of extracting a fluid sample from the adjacent formation comprises the step of extracting a plurality of samples from the adjacent formation until the resistivity of each sample is substantially the same.

8. A downhole tool for analyzing fluids contained in a formation traversed by a well bore comprising:

a housing;

means for extracting a fluid sample from a formation adjacent said housing when said housing is received in a well bore, said extracting means being mounted on said housing; and a chromatograph received in said housing for generating information relating to the composition of such a sample.

9. The tool of claim 8 wherein said tool further includes means for transmitting such information to the surface.

10. The tool of claim 8 wherein transmitting means comprises a microprocessor.

11. The tool of claim 8 wherein said extracting means includes a purging chamber for receiving such a sample.

12. The tool of claim 11 wherein said tool further includes:

a chromatograph sample chamber operatively connected to said chromatograph; and means for placing said purging chamber in fluid communication with said chromatograph sample chamber.

13. The tool of claim 12 wherein said tool further includes:

a reservoir for holding solvent; and means for placing said solvent reservoir in fluid communication with said chromatograph sample chamber.

14. The tool of claim 13 wherein said tool further includes means for withdrawing fluid from said solvent reservoir and means for injecting such withdrawn fluid into said chromatograph sample chamber.

15. A method for obtaining multiple fluid sample analyses from fluid contained in a formation traversed by a well bore, said method comprising the steps of:

lowering a chromatograph to a first selected level in the well bore;

extracting a fluid sample from the adjacent formation;

placing the fluid sample in a chromatograph sample chamber;

forcing the fluid sample from the chromatograph sample chamber into the chromatograph thereby generating information relating to the composition of the fluid sample;

purging the chromatograph sample chamber with a solvent;

moving the chromatograph to another location at a second level in the well bore; and at the second location, repeating the steps of the method performed at said first selected level for extracting a fluid sample and generating information relating to the composition thereof.

16. The method of claim 15 wherein the step of extracting a fluid sample from the adjacent formation comprises the step of extracting a plurality of samples from the adjacent formation until the resistivity of each sample is substantially the same.

17. The method of claim 15 wherein said method further includes the step of combining the fluid sample with a solvent prior to forcing the fluid sample into the chromatograph.

18. Apparatus for obtaining multiple fluid sample analyses from fluid contained in a formation traversed by a well bore, said apparatus comprising:

a housing;

a formation tester mounted on said housing for obtaining a formation fluid sample;

a chromatograph received in said housing for generating information relating to the composition of such a fluid sample;

a chromatograph sample chamber operatively connected to said chromatograph for receiving such a fluid sample from said formation tester and providing the same to said chromatograph; and a solvent reservoir operatively connected to said chromatograph sample chamber for purging said sample chamber with solvent after a fluid sample therein is provided to said chromatograph.

19. The apparatus of claim 18 wherein said apparatus further includes:

a first valve between said formation tester and said chromatograph sample chamber;

a second valve between said solvent reservoir and said chromatograph sample chamber; and a third valve between said chromatograph sample chamber and said chromatograph.

20. The apparatus of claim 19 wherein said apparatus further includes:

means for detecting the resistivity of a fluid sample in said formation tester; and a microprocessor operatively connected to said detecting means and to said valves, said microprocessor being programmed to open said first valve after said resistivity stablizes and thereafter to close said first valve, and to open said second and third valves.

* * * * *